United States Patent [19]

Box et al.

[11] Patent Number: 4,526,038
[45] Date of Patent: Jul. 2, 1985

[54] CROSS-FLOW ULTRASONIC TRANSDUCER HEAD

[75] Inventors: William A. Box, Bethel Park; Eugene R. Rusiecki, Monroeville, both of Pa.

[73] Assignee: United States Steel Corporation, Pittsburgh, Pa.

[21] Appl. No.: 579,630

[22] Filed: Feb. 13, 1984

[51] Int. Cl.³ ............................................. G01N 29/04
[52] U.S. Cl. ................................................. 73/644
[58] Field of Search .......................... 73/644, 629, 632

[56] References Cited

U.S. PATENT DOCUMENTS

| | | | |
|---|---|---|---|
| 2,992,553 | 7/1961 | Joy | 73/644 |
| 3,218,846 | 11/1965 | Joy | 73/644 |
| 3,420,097 | 1/1969 | Battermann et al. | 73/644 |
| 3,485,088 | 12/1969 | O'Connor | 73/644 |
| 3,745,833 | 7/1973 | Armstrong | 73/644 |
| 3,777,554 | 12/1973 | Papay et al. | 73/644 |
| 4,033,178 | 7/1977 | Holt et al. | 73/644 |

FOREIGN PATENT DOCUMENTS

| | | | |
|---|---|---|---|
| 0462187 | 10/1974 | U.S.S.R. | 73/644 |
| 0596917 | 2/1978 | U.S.S.R. | 73/632 |

Primary Examiner—Anthony V. Ciarlante
Attorney, Agent, or Firm—George D. Dickos

[57] ABSTRACT

Apparatus to prevent the deposition of dirt and fine air bubbles on the flat end of a piezo-electrical crystal transducer that emits and receives ultrasonic waves consists of a body having an internal passage that angularly directs water in sweeping relation to the flat end of the crystal to keep it cleansed of air bubbles, dirt or scum. A portion of the so-directed water is diverted angularly to and away from the crystal end to thereby produce a pressure at the transducer end of sufficient magnitude to suppress the generation of air bubbles. Part of the entering water enters a vertical water column that couples the transducer to the object being measured while the cleansing portion of the stream is re-directed back into the apparatus to join that in the vertical column to create a water jet of essentially uniform velocity distribution.

5 Claims, 2 Drawing Figures

4,526,038

CROSS-FLOW ULTRASONIC TRANSDUCER HEAD

DESCRIPTION OF THE INVENTION BACKGROUND

The present invention relates to apparatus for use in ultrasonic testing and, in particular, to an apparatus for providing a fluid coupling between a piezo-electric crystal transducer element and a test body.

In the inspection of a test body by ultrasonic techniques, ultrasonic waves are generated by the transducer, directed at the test body and reflected therefrom back to the transducer so that the time differential between pulses may be used to ascertain various features of the test body. As can be readily appreciated, it is essential for the ultrasonic energy to be efficiently coupled between the transducer and the test body. One fairly effective but problem-ridden method of providing a coupling comprises interposing a water column between and in intimate contact with both the transmitting-receiving face of the transducer and the surface of the test body. In the past, the means for performing an ultrasonic type of inspection generally included a housing for forming a column of a coupling fluid to flow between the transducer and the workpiece.

A primary area of concern with such a coupling means is that foreign matter becomes accumulated on the operative end of the transducer. In particular, with time in service dirt, e.g., mud, scum and solids, and fine air bubbles become deposited on the flat surface of a transducer during the use of such a system. The material deposited on the surface of the transducer causes a deterioration of the signal which subsequently causes such signal to be lost in the electrical circuit noise caused by the deposits.

Accordingly, it is an object of this invention to provide an ultrasonic testing apparatus which obviates the disadvantageous phenomena reported above and yet enables effective fluid coupling between the transducer and the test body.

It is a further object to provide such a device in which there is an elimination of dirt and air bubbles from the surface of the transducer which permits an accurate testing and inspection of the test body.

SUMMARY OF THE INVENTION

In accordance with the present invention, there is provided apparatus for generating a fluid coupling between an ultrasonic transducer and a test body which eliminates foreign materials from the surface of such transducer. The fluid coupling unit provided herein includes a housing mounting the ultrasonic transducer at an end thereof remote from a body under test. A substantially straight axial longitudinal flow passage is included in the housing having a discharge path directed toward the test body. A first transverse passageway is included in said housing to angularly direct most of the coupling liquid in sweeping relation to the operative end of the transducer and the remainder of the coupling fluid along the axial longitudinal flow passage. Such first transverse passageway terminates adjacent to the transducer and to the longitudinal flow path. A second transverse passageway is included in the housing radially opposite from the first transverse passageway and also terminates adjacent the transducer. The first and second passageways are configured to cause the coupling fluid to impinge and be angularly diverted away from the operative end of the transducer to produce an increase in pressure at such operative end of sufficient magnitude to suppress the generation of bubbles on the transducer surface and to remove any foreign matter therefrom. In addition, a toroidal chamber is provided in the housing surrounding the longitudinal flow passage between the end of said housing adjacent the body under test and the transducer. The toroidal chamber is provided with an inlet on one side of the housing and an inwardly radially directed outlet. Further, a converging cavity is provided in the housing which is disposed about the longitudinal passageway and is operative to tangentially receive flow from the outlet of the toroidal chamber and to join such flow with that from the longitudinal passageway. Finally, a conduit is provided to direct coupling fluid between the second transverse passageway and the inlet of the toroidal chamber.

In operation, coupling fluid is introduced into the first passageway and a portion of it enters the axial longitudinal flow passage; however, a predominant portion of the flow from the first passageway angularly sweeps across the transducer surface thereby removing foreign matter and suppressing bubbles and enters the second passageway. From this point, the coupling fluid from the second passageway is directed into the toroidal chamber. At this point, fluid exiting from the toroidal chamber enters the converging passageway and is combined tangentially with flow from the longitudinal passageway. The flow then exits the housing and is directed onto the test piece.

The subject invention is directed toward an improved means for providing a fluid coupling between an ultrasonic transducer and a test body which eliminates the inclusion of foreign particles and air bubbles on the transducer surface thereby overcoming, among others, the above-discussed problems and provides an apparatus which is effective in ultrasonic inspection.

These and other details, objects and advantages of the invention will become apparent as the following description of the present preferred embodiment thereof proceeds.

BRIEF DESCRIPTION OF THE DRAWINGS

In the accompanying drawings, we have shown a present preferred embodiment of the invention wherein.

DETAILED DESCRIPTION OF THE INVENTION

Figure 2:
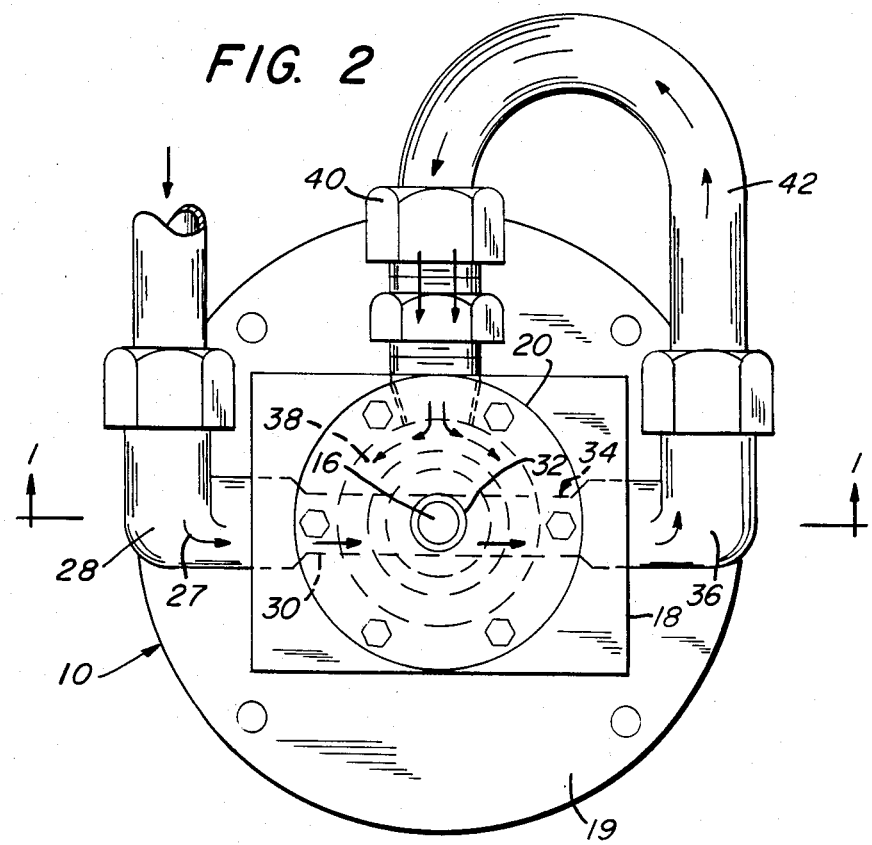

Referring now to the drawings wherein the showings are for purposes of illustrating the present preferred embodiment of the invention only and not for purposes of limiting same, the figures show an apparatus 10 for providing a fluid coupling between an ultrasonic piezo-electric transducer 12 and a test body 14.

Figure 1:
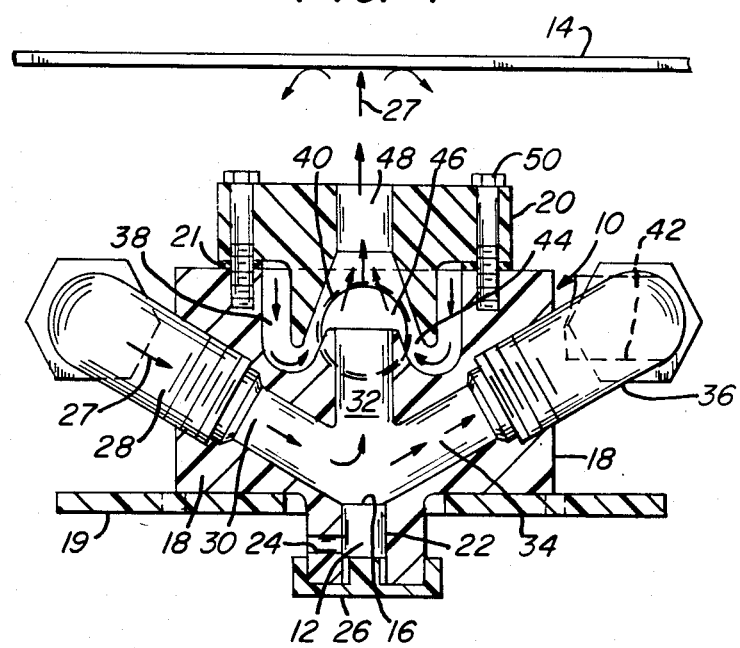
FIG. 1 is a front elevation cutaway view of a fluid coupling apparatus according to the present invention taken along line 1—1 of FIG. 2; and, FIG. 2 is a plan view showing hidden lines of the fluid coupling apparatus provided herein.

More particularly and with reference to FIG. 1, there is shown an operative end 16 of the transducer 12. The coupling apparatus housing preferably includes a lower 18 and upper 20 sections. Lower coupling body 18 and upper body 20 are preferably constructed of a non-magnetic material such as plastic. The provision of such a material would assist in the reduction of unwanted electrical noise in the circuitry. A flange 19 may be provided to be affixed to lower surface of lower body portion 18 to attach apparatus 10 to a fixed mounting point. In addition, a gasket 21 may be provided between upper body member 20 and lower body 18. Lower body 18 is provided with axial bore 22 adapted to longitudinally receive the transducer 12. Slot 24 is provided in the lower surfaces of part 18 so as to provide access for electrical wires to transducer 12. End cap 26 is provided on the lowermost end of lower body 18 to withhold transducer element 12 within body 18.

The liquid coupling medium 27, which may consist of water or other suitable coupling fluid, is introduced from a pressurized source, not shown, into lower body member 18 by means of inlet fitting 28. Fitting 28 may be adapted to be threaded into lower body member 18 or may be formed as an integral part thereof. Inlet fitting 28 communicates with the first transverse passageway 30 which consists of a bore in lower member 18. Passageway 30 is configured as a bore within lower body 18 which is radially and angularly disposed with respect to transducer surface 16 in order to cause a sweeping flow across said surface 16 and increase the pressure on such surface 16. From first passageway 30, a portion of the coupling fluid 27 enters the axial longitudinal passage 32 while the remaining coupling fluid 27 which sweeps across surface 16 enters the second angularly disposed, radial, tranverse passageway 34. The axial longitudinal bore 32 is provided to generate a low pressure fluid column between transducer surface 16 and test body 14 and, hence, causes the coupling fluid to be directed between the transducer surface 16 and the test body 14 to effectively transmit the ultrasonic impulses. The second transverse passageway 34 as described above is provided to accept the flow of the coupling fluid 27 from passageway 30 and angularly direct the coupling fluid 27 away from the transducer surface. Preferably, passageways 30 and 34 are disposed at an angle of less than forty-five degrees (45°) and more preferably approximately of thirty degrees (30°), respectively, with respect to transducer surface 16. While the angle of thirty degrees (30°) is preferable, we have found that the utilization of angles less than or in excess of forty-five degrees (45°) provides suitable results. In addition, it is preferable that passageways 30 and 34 be disposed at approximately equal angles with respect to the transducer surface 16. Coupling fluid entering second transverse passageway 34 is caused to exit lower body member 18 via fitting 36 which may be formed as an integral part of lower body member 18.

Also provided in the upper portion of lower body member 18 is toroidal chamber 38 which is created by the cavity formed between lower body member 18 and upper body member 20 and surrounds axial longitudinal passageway 32. Toroidal chamber 38 is provided with an inlet fitting 40 which receives flow from second passageway 34 by means of conduit 42. Coupling fluid 27 which enters toroidal chamber 38 exits that area by means of radially inwardly directed, curved flow passage 44 formed between the lower regions of upper body 20 and lower body member 18. Flow through radially inwardly directed passage 44 enters converging area 46 which tangentially joins the fluid flows from longitudinal passageway 32 and from the toroidal chamber 38 via passage 44, hence, rejoining all of the liquid 27 which originally entered via first passageway 30. The coupling fluid 27 is then directed out of the apparatus 10 and against the surface of the test body 14 via exit bore 48 which is also the termination of bore 32. In order to restrainably join lower body member 18 and upper body member 20, screws 50 are provided to be threaded through upper member 20 and into lower body portion 18.

In operation, as is apparent from the above presented description of the invention, liquid coupling medium 27 enters the apparatus 10 via fitting 28 and is caused to flow into first passageway 30. At this point, some of the liquid coupling medium 27 is directed along axial longitudinal bore 32 while most of the liquid coupling fluid 27 is angularly directed across the transducer surface 16 in sweeping relation thereto so as to increase the pressure on surface 16 and suppress air bubble formation and to remove other foreign particles which may have become entrained on transducer surface 16. Such liquid 27 which sweeps across transducer surface 16 is angularly diverted into second transverse passageway 34 and exits the lower body member 18 by means of fitting 36. The portion of the coupling fluid 27 so removed is caused to reenter the lower body member 18 via conduit 42 which communicates by means of fitting 40 with toroidal chamber 38. At this point, the liquid coupling medium 27 is directed about chamber 38 and into converging area 46 by means of radially converging channel 44. While in chamber 46, the flows from the longitudinal passageway 32 and second transverse passageway 34 are joined tangentially and caused to exit upper body member 20 via exit bore 48. Coupling fluid 27 flow from bore 48 is directed onto the surface of the test body 14 forming a uniform fluid column between the transducer surface 16 and the test body 14.

Accordingly, the present invention provides a means to remove foreign materials from the surface of piezoelectric crystal transducer 16 provides a soft fluid coupling along longitudinal bore 32 and removes foreign objects from the transducer surface 16 by the angular diversion of the coupling liquid 27 from passage 30 to passageway 34.

It will be understood that various changes in the details, materials and arrangements of parts which have been hereindescribed and illustrated in order to explain the nature of the invention may be made by those skilled in the art within the principle and scope of the invention as expressed in the appended claims.

What is claimed is:

1. In ultrasonic testing equipment, apparatus for forming and flowing a uniform stream of coupling liquid between a piezo-electric crystal transducer and a test body, said apparatus comprising:

(a) a housing mounting said transducer at an end thereof remote from said test body and providing a substantially straight axial longitudinal flow passage from said transducer and having a discharge path directed toward said body;

(b) a first transverse passageway in said housing radially intersecting said axial longitudinal passageway adjacent said transducer, said first passageway being configured to angularly direct said liquid in sweeping relation to the operative end of said transducer;

(c) a second transverse passageway in said housing radially opposite from said first transverse passageway and intersecting said first passageway adjacent the operative end of said transducer, said second passageway being configured to divert said fluid angularly away from the operative end of said transducer to produce an area of increased pressure at said operative end of said transducer so as to suppress the generation of bubbles on said surface;

(d) a toroidal chamber in said housing surrounding said axial longitudinal flow passage between the end of said housing adjacent said test body and said transducer, said toroidal chamber having an inlet on one side of said body and an inwardly directed radial outlet;

(e) a converging cavity in said housing disposed about said axial longitudinal passageway and operative to combine the flows from the outlet of said toroidal chamber and from said longitudinal passageway; and, (f) a conduit to direct said fluid between said second transverse passageway and the inlet of said toroidal chamber.

2. The apparatus of claim 1 in which the included angle between said first transverse passageway and the plane of the operative end of said transducer is greater than 0° but less than 45°.

3. The apparatus of claim 2 in which the included angle between said first transverse passageway and the plane of the operative end of said transducer is approximately 30°.

4. Apparatus of claim 3 in which the included angles between the first and second passageways and the plane of the operative end of said transducer are approximately equal.

5. Apparatus of claim 4 in which the inwardly directed radial outlet of said toroidal chamber is configured so as to direct flow of said coupling fluid from said toroidal chamber into said converging cavity approximately parallel to said axial longitudinal passageway.

* * * * *